United States Patent [19]

Montana

[11] Patent Number: 5,895,870
[45] Date of Patent: Apr. 20, 1999

[54] TUBE SHEET RETRACTABLE PROBE

[75] Inventor: Richard A. Montana, Evington, Va.

[73] Assignee: Framatome Technologies, Inc., Lynchburg, Va.

[21] Appl. No.: 08/863,157

[22] Filed: May 27, 1997

[51] Int. Cl.⁶ .................. G01N 17/04; G01M 19/00
[52] U.S. Cl. .......................................... 73/866.5
[58] Field of Search ........................ 73/866.5, 86

[56] References Cited

U.S. PATENT DOCUMENTS

| | | | |
|---|---|---|---|
| 4,471,651 | 9/1984 | Dimeff et al. | 73/40.5 R |
| 4,505,323 | 3/1985 | de la Pintiere et al. | 165/11.2 |
| 4,779,450 | 10/1988 | Kempf et al. | 73/49.2 T |
| 4,841,787 | 6/1989 | Waterman | 73/866.5 |
| 4,854,302 | 8/1989 | Allred, III | 600/109 |
| 4,959,639 | 9/1990 | Benson | 340/618 |
| 5,106,580 | 4/1992 | Mudiam | 422/53 |
| 5,174,325 | 12/1992 | Okel et al. | 137/317 |
| 5,210,533 | 5/1993 | Summers et al. | 73/152.54 X |
| 5,303,602 | 4/1994 | Morgan | 73/866.5 |
| 5,398,560 | 3/1995 | Zollingger et al. | 73/865.8 |
| 5,402,454 | 3/1995 | Eckardt | 376/245 |
| 5,408,883 | 4/1995 | Clark, Jr. et al. | 73/601 |
| 5,504,788 | 4/1996 | Brooks et al. | 376/248 |
| 5,756,908 | 5/1998 | Knollmeyer et al. | 73/866.5 |

*Primary Examiner*—Thomas P. Noland
*Attorney, Agent, or Firm*—Rhodes Coats & Bennett, L.L.P.

[57] ABSTRACT

A retractable probe for placing and removing corrosion coupons from a steam generator during chemical cleaning of the steam generator, the chemical process occurring at a relatively high pressure and temperature. The probe includes a series of inner-linked and hinged sections which may be manipulated to insert the probe within and through the various structures of the steam generator, including the shell and shroud, while avoiding contact with tie rods and blow down lines and facilitating easier operation within the tight confines of the barriers surrounding the generator system. A bendable Teflon® rod is used to withdraw the coupon through the differently angled sections of the probe and eventually through the nozzle opening or man-hole of the shell. A selectively openable valve is utilized in combination with a packing gland. This combination allows the coupon to be removed while the steam generator is being cleaned or operated.

26 Claims, 3 Drawing Sheets

5,895,870

1

TUBE SHEET RETRACTABLE PROBE

BACKGROUND OF THE INVENTION (1) Field of the Invention

The present invention relates generally to the inspection of nuclear steam generators and, more particularly, to a retractable probe assembly for placing monitoring devices near areas difficult to access during a chemical cleaning operation, such as a tube support plate of the generator, and removing those devices while the generator is being cleaned under process temperature and pressure.

(2) Description of the Prior Art

A nuclear steam generator typically includes a shell spaced apart from and surrounding an inner shroud. The shroud surrounds the tie rods, tubes, tube support plates and a tube sheet therein. The vessel's tie rods are within and run parallel to the shroud and tubes. Generally, the shell has an opening with a nozzle neck extending therefrom. The nozzle neck is equipped with an annular flange. The opening is usually above a tube support plate or a tube sheet. The shroud includes an opening substantially aligned with the opening of the shell and the nozzle neck.

Because of the build up of corrosion during normal operation, it is necessary to periodically chemically clean and/or monitor corrosion in the generator. The condition of the area around the upper surface of the tube support plate and/or the tube sheet and the inner walls of the shroud near these regions should be monitored during the chemical cleaning process to determine an amount of corrosion to assess the structural integrity, project vessel life and evaluate vessel health.

A major obstacle for such cleaning and monitoring processes is the absence of a probe positioner capable of reaching the tube support plate or tube sheet through the nozzle neck opening without having the monitoring device contact the tie rods or other structures within the shroud. Contacting these structures with a monitoring device may result in damage to the monitoring device and may result in erroneous readings. The difficulty in reaching the tube support plate or tube sheet with the monitoring device is that the monitoring device must be placed through the nozzle neck and across the gap between the shroud and the shell into the inside of the shroud and then drop immediately downward to avoid contact with the tie rods.

The difficulty in placing a monitor near the tube support plate given the above described obstacles was addressed in a patent application for a probe positioner, U.S. Ser. No. 08/679,966, filed Jul. 15, 1996, now U.S. Pat. No. 5,756,908 to Knollmeyer et al. The Knollmeyer et al. patent provides for actively monitoring these hard to reach areas electronically while the generator is off-line.

The Knollmeyer et al. patent does not provide the ability to passively monitor the vessel, with devices such as corrosion coupons, while the generator is on-line. Therefore, there remains a need to place passive monitoring devices in difficult to access areas within the vessel, subject the monitoring devices to the vessel environment at high temperatures and pressure and remove the monitoring devices for inspection while the generator is on-line.

Metal Samples Company of Munford, Ala., has developed a rigid guide structure and an inflexible rod associated with a packing gland for removing coupons while the generator is on-line. However, this system is incapable of placing or removing coupons below the shell nozzle or opening and does not address the problem presented by the barrier

2 placement about the shell. Applicant is unaware of any system capable of maneuvering monitoring devices into difficult to reach areas and providing removal of these devices without breaching the sealed environment of an operating generator or boiler. Thus, there remains a need for a new and improved probe system which is capable of providing for the removal of monitoring devices from hard to access areas within generator tubing while, at the same time, without breaching the pressurized, sealed environment therein.

SUMMARY OF THE INVENTION

The present invention is directed to a retractable probe for placing and removing corrosion coupons from a steam generator during chemical cleaning of the steam generator, the chemical process occurring at a relatively high pressure and temperature. The invention incorporates a series of inner-linked and hinged sections which may be manipulated to insert the probe within and through the various structures of the steam generator, including the shell and shroud, while avoiding contact with tie rods and blow down lines and facilitating easier operation within the tight confines of the barriers surrounding the generator system.

A Teflon® rod is used to withdraw the coupon through the differently angled sections of the probe and eventually through the nozzle opening or man-hole of the shell. The Teflon® rod is bendable so that it may follow the contours of the probe, thereby allowing removal of coupons even when the probe is used in tight spaces. The Teflon® rod is further advantageous because it is impervious to all presently known chemicals used in the cleaning process, withstands high temperatures and has a low coefficient of friction. Preferably, the rod is of a commercially available, 100% Teflon® construction.

A selectively openable valve is utilized in combination with a packing gland. This combination allows the coupon to be removed while the steam generator is being cleaned. The valve is opened to allow the Teflon® rod to be inserted into the steam generator and withdrawn. The packing gland surrounds the Teflon® rod downstream of the valve and prevents leakage of the fluids from the cleaning process. Once the coupon is removed, the valve is closed and any fluid captured in the probe between the valve and the packing gland is drained. At this point, the coupons are outside of the sealed generator system and accessible for inspection.

Accordingly, one aspect of the present invention is to provide a retractable probe assembly for monitoring difficult to access areas in an substantially enclosed system, the probe assembly having: (a) a flexible rod and guide system including: (i) a flexible tubular guide adapted to extend through one or more barrier openings and downward along one of the barriers to an area to monitor in the enclosed system; and (ii) a flexible rod retractively insertable within the guide and adapted to extend through the guide having a mount for a removable monitoring device; and (b) a receiving assembly sealably engaging the guide system and having an interior path to guide removal of the rod from the guide, the receiving assembly adapted to receive the monitoring device when removed by the rod.

Another aspect of the present invention is to provide a flexible guide system for a retractable probe assembly for monitoring difficult to access areas in an substantially enclosed system, the guide system having: (a) a first tubular link, a second tubular link and a third tubular link; (b) a first hinge pivotally connecting the first and second link; and (c)

a second hinge pivotally connecting the second and third link, the first and second hinge adapted to provide: (i) a first guide orientation adapted to maintain the links of the guide in straight alignment while being held horizontally and allow the links to pivot about the hinges when the guide is axially rotated out of the first guide orientation; and (ii) a second guide orientation adapted to allow the second and third link to downwardly align along the inner wall; wherein the guide is adapted to remain in the first guide orientation while being horizontally placed through an opening in the inner and outer substantially vertically oriented wall and pivot downwardly at each the hinge along the inner wall as the guide is rotated from the first guide orientation to the second guide orientation without fully horizontally extending past the second wall.

Still another aspect of the present invention is to provide a retractable probe assembly for monitoring difficult to access areas in an substantially enclosed system, the probe assembly having: (a) a flexible rod and guide system including: (i) a flexible tubular guide adapted to extend through one or more barrier openings and downward along one of the barriers to an area to monitor in the enclosed system, the guide including: a first tubular link, a second tubular link and a third tubular link; a first hinge pivotally connecting the first and second link; and a second hinge pivotally connecting the second and third link, the first and second hinge adapted to provide: a first guide orientation adapted to maintain the links of the guide in straight alignment while being held horizontally and allow the links to pivot about the hinges when the guide is axially rotated out of the first guide orientation; and a second guide orientation adapted to allow the second and third link to downwardly align along the inner wall; wherein the guide is adapted to remain in the first guide orientation while being horizontally placed through an opening in the inner and outer substantially vertically oriented wall and pivot downwardly at each hinge along the inner wall as the guide is rotated from the first guide orientation to the second guide orientation without fully horizontally extending past the second wall; and (ii) a flexible rod retractively insertable within the guide and adapted to extend through the guide having a mount for a removable monitoring device; (b) a receiving assembly sealably engaging the guide system and having an interior path to guide removal of the rod from the guide, the receiving assembly adapted to receive the monitoring device when removed by the rod; and (c) a packing gland axially connected to the receiving assembly and adapted to moveable engage and seal between the flexible rod and the receiving assembly, the packing gland sealing off the interior of the receiving assembly on an end opposite of the guide system.

These and other aspects of the present invention will become apparent to those skilled in the art after a reading of the following description of the preferred embodiment when considered with the drawings.

DESCRIPTION OF THE PREFERRED EMBODIMENTS

Figure 1:
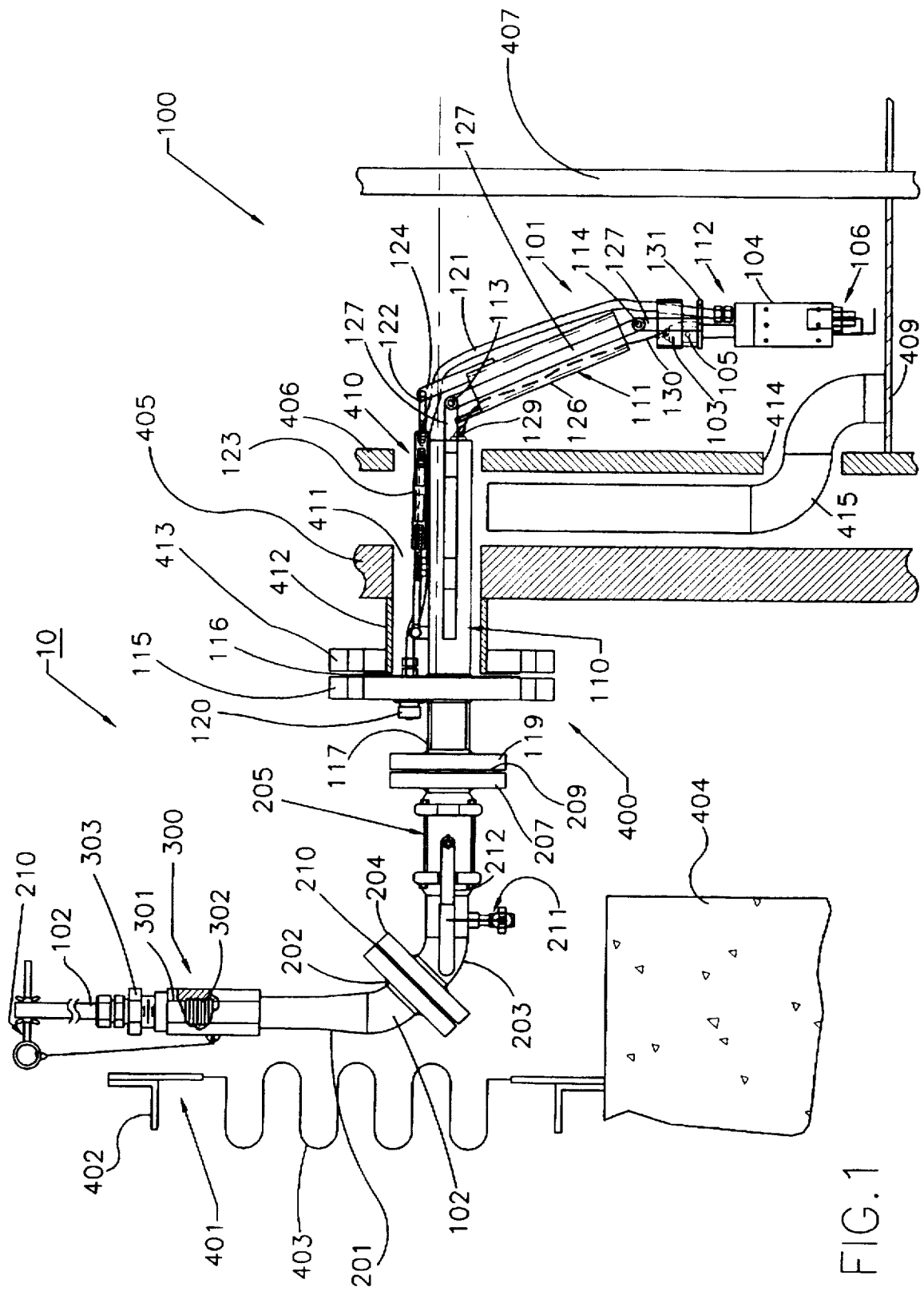
FIG. 1 is a partial cross-sectional view of the tube sheet retractable probe assembly mounted within a boiler environment constructed according to the present invention.

In the following description, like reference characters designate like or corresponding parts throughout the several views. Also in the following description, it is to be understood that such terms as "forward", "rearward", "left", "right", "upwardly", "downwardly", and the like are words of convenience and are not to be construed as limiting terms.

Referring to the drawings in general and FIG. 1 in particular, it will be understood that the illustrations are for the purpose of describing a preferred embodiment of the invention and are not intended to limit the invention thereto. As best seen in FIG. 1, a retractable probe assembly, generally designated 10, is shown constructed according to the present invention. The retractable probe assembly 10 includes three major sub-assemblies: a rod and guide assembly 100; a receiving assembly 200; and a packing gland assembly 300. The steam generator environment is generally referenced as 400.

Throughout the life of nuclear steam generators, various types of corrosion monitoring is required within the generator. Unfortunately, the areas requiring monitoring are very difficult to access given the steam generator environment 400 and the structural design and location of the items requiring monitoring. The steam generator environment 400 shown in FIG. 1 is exemplary of the obstacles facing a system operator when attempting to properly monitor for corrosion. To exacerbate the situation, it is often preferable to monitor for corrosion while the generator is undergoing a chemical cleaning operation.

The steam generator environment 400 typically includes a barrier wall 401 surrounding and completely encompassing the generator vessel and, more importantly, restricting the area within which the vessel access nozzles may be accessed. The barrier wall 401 may include a rigid barrier wall portion 402 in conjunction with a corrugated, semi-flexible wall 403, both of which are built upon a foundation 404. The vessel generally comprises an outer shell 405 encircling and spaced away from an inner shroud 406. Tie rods 407 are located within and run vertically and parallel with the interior of the shroud 406. The shroud 406 encompasses a tube sheet 409 having a radially extending floor through which the tie rods 407 and tubes (not shown) extend. Above the tube sheet 409, the shroud 406 includes a shroud opening 410 aligned with a shell opening 411 within the shell 405. A shell nozzle 412 extends outward from the shell opening 411 to a nozzle flange 413.

Access to the inner portions of the shroud 406 is gained through the shroud opening 410, the shell opening 411, the shell nozzle 412 and the nozzle flange 413. In certain situations, the steam generator environment 400 is further convoluted by the presence of a blow down line 415 extending downwardly between the shell 405 and the shroud 406, and through a blow down opening 414 into the shroud 406 to the tube sheet 409. The blow down line 415 is used to inject nitrogen or other inerting gases into the system to remove remaining water from the system during cleaning or as otherwise necessary during steam generator shutdowns.

In order to effectively monitor corrosion in the steam generator environment 400 described above, it is necessary to remotely operate a corrosion monitoring system given the physical constraints of the barrier wall 401 and the shell 405. Furthermore, the monitoring device must be capable of extending through the shell opening 411 and the shroud opening 410 before extending downwardly to a position just above the tube sheet 409. Importantly, any monitoring device so positioned must not come in contact with the blow down line 415 or the multiple tie rods 407.

The first objective is to place the monitoring device near the tube sheet 409 or similar difficult to reach location within the vessel given the limited areas of access. In the case of the steam generator environment 400 depicted in FIG. 1, access is gained through the shell nozzle 412. Once the monitoring device is in place, either data from the device must be read remotely or the device itself must be removed and analyzed.

Monitoring for corrosion when the generator is undergoing a chemical cleaning process is preferable. The description which follows details a preferred embodiment providing for the placement of a monitoring device in difficult to access portions of the tubing and removing the monitoring device without taking the generator off-line or otherwise deactivating that particular portion of vessel being monitored.

In the preferred embodiment, the rod and guide assembly 100 includes a guide arm 101 and a flexible rod 102 and is adapted to safely place a coupon holder 103 or other electronic monitoring system 104 in the area requiring monitoring. The coupon holder 103 generally has coupons 105 which passively monitor corrosion or other chemically related conditions present within the monitoring environment. These coupons react in a known manner to various conditions present within the monitoring environment.

When the coupons are removed from the environment within the generator vessel, they are analyzed to determine the corrosion characteristics associated with either cleaning or the normal operation of the steam generator, as the case may be. For the purposes of the discussion here, coupons 105 measure corrosion but other operating environmental variables could also be measured.

In order to place the coupons 105 or any other electronic monitoring device 104 near the tube sheet 409 the guide arm 101 must allow for the monitoring end 106 to extend through and beyond the shell opening 411 and the shroud opening 410 before flexing downward to avoid contact with the tie rod 407, yet extend far enough into the shroud 406 to avoid contact with the blow down line 415.

Preferably, the guide arm 101 is composed of three tubular links: a first link 110, a second link 111 and a third link 112. A first hinge 113 hingably connects the first and second links 110, 111 while a second hinge 114 hingably connects the second and third links 111, 112. The coupon holder 103 and coupons 105 are attached to rod 102 by wire or cable 130. The electronic monitoring device 104 is generally mounted along the third link 112. The third link 112 may or may not require a tubular configuration depending on the application and placement of the coupon 105 or electronic monitoring device 104.

The first link 110 includes a mounting flange 115 designed to mount to the nozzle flange 413 of the shell 405. Preferably, a nozzle seal gasket 116 is placed between these flanges during monitoring. A portion of the first link 110 extends past the mounting flange 115 and forms exit tubing 117 having an exit tubing flange 119 designed to engage the receiving assembly 200 discussed in greater detail below. The mounting flange 115 includes a hermetically sealed electrical connector 120 to enable electrical connection to the electronic monitoring device 104 via the monitor cabling which is enclosed in flexible conduit 121.

In order to properly place the monitoring devices, the guide arm 101 must remain rigid during initial insertion through the shell nozzle 412, the shell opening 411 and the shroud opening 410. Once the third link 112 is sufficiently past the shroud opening 410, the second and third links 111, 112 must begin bending downwardly at the first and second hinges 113, 114 toward the tube sheet 409. As previously noted, the guide arm 101 must extend into the shroud 406 and bend downward without contacting any of the tie rods 407. To facilitate such insertion, the first hinge 113 and the second hinge 114 are adapted and oriented in a manner allowing the guide arm links 110, 111, 112 to remain straight while being held in a horizontal position. Furthermore, the hinges 113, 114 allow the links 110, 111, 112 to pivot about the hinges 113, 114 once the guide arm is rotated away from the position where the links are held in a straight, horizontal orientation.

The hinges 113, 114 are aligned in a manner to allow the links 110, 111, 112 to pivot in a common plane. However, the hinges 113, 114 may have varying orientations to allow pivoting about a particular hinge 113, 114 to start at various points during rotation of the guide arm 101. For example, the second hinge 114 may have an orientation allowing the third link 112 to begin pivoting at an initial, or early point, during rotation while the first hinge 113 would not allow the second link 111 to start pivoting until the guide arm 101 is rotated past a second point during the rotation.

Attention is directed to the disclosure for the application of Knollmeyer et al., Ser. No. 08/679,966, filed on Jul. 15, 1996, which is hereby incorporated by reference in its entirety. Particular attention is drawn to the pivoting action shown in FIGS. 3–6 and the corresponding discussion in that application.

Preferably, the guide arm 101 includes a lock rod 122 connected between the first link 110 and the second link 111 in order to adjustably position the second link a prescribed position relative to the first link 110 once the device is installed. In order to accomplish, the lock rod 122 includes a turnbuckle 123 configured to set a maximum length to which the lock rod 122 may extend. The turnbuckle 123 also allows for the compression or reduction, of the length of the lock rod 122 when the first link 110 and the second link 111 are in a final position. The rod is not initially connected. Its connection is completed when installation is completed to "lock" link ill's position relative to link 110 to avoid any "pendulum-type" motion.

Preferably, the lock rod 122 includes a lock rod tab and hinge 124 extending from the second link 111. This configuration provides for the aforementioned limited pivoting action without obstructing the area between the first and second links 110, 111.

Figure 2:
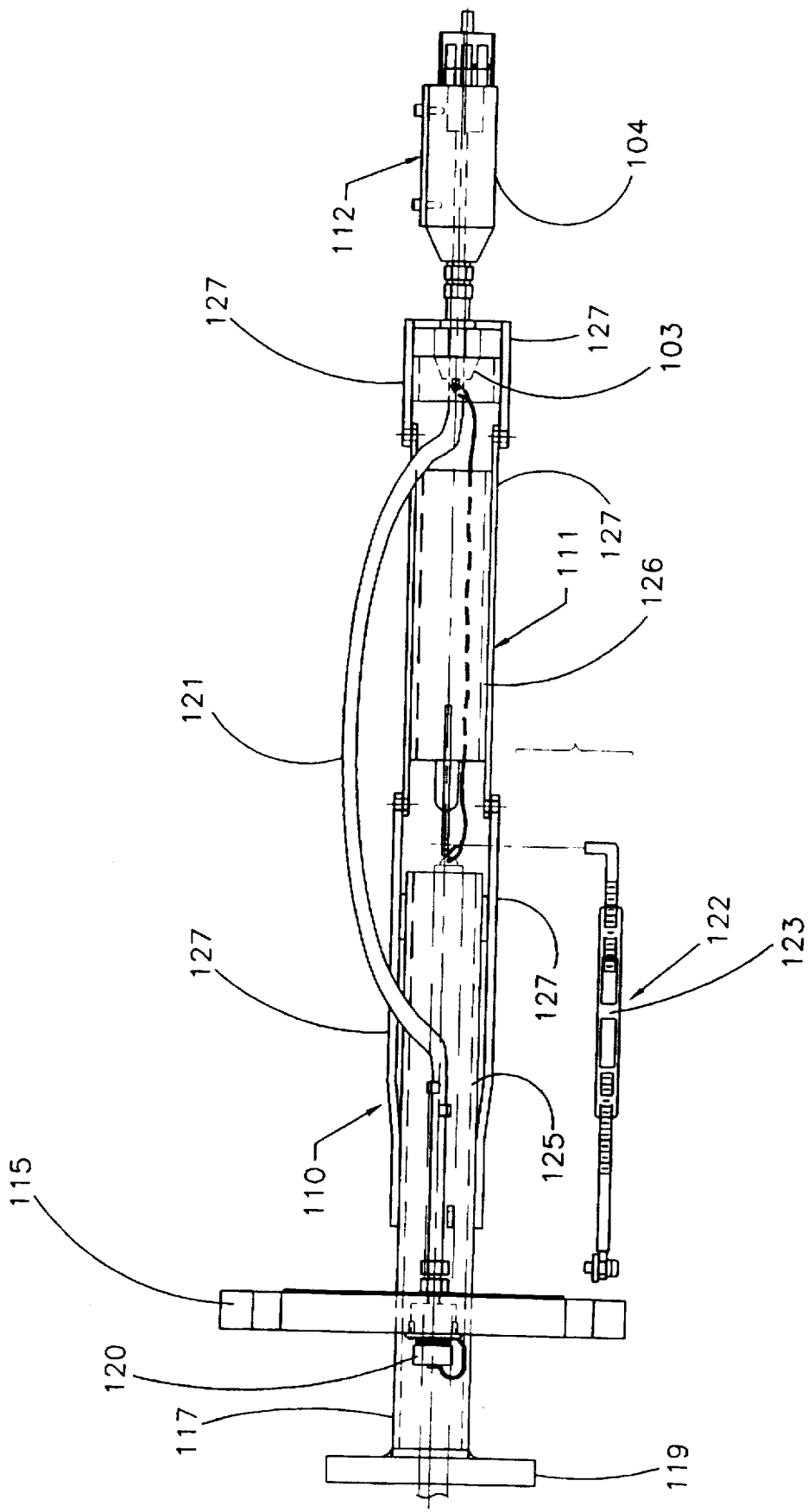
FIG. 2 is a top view of the guide assembly shown in FIG. 1.
Figure 3:
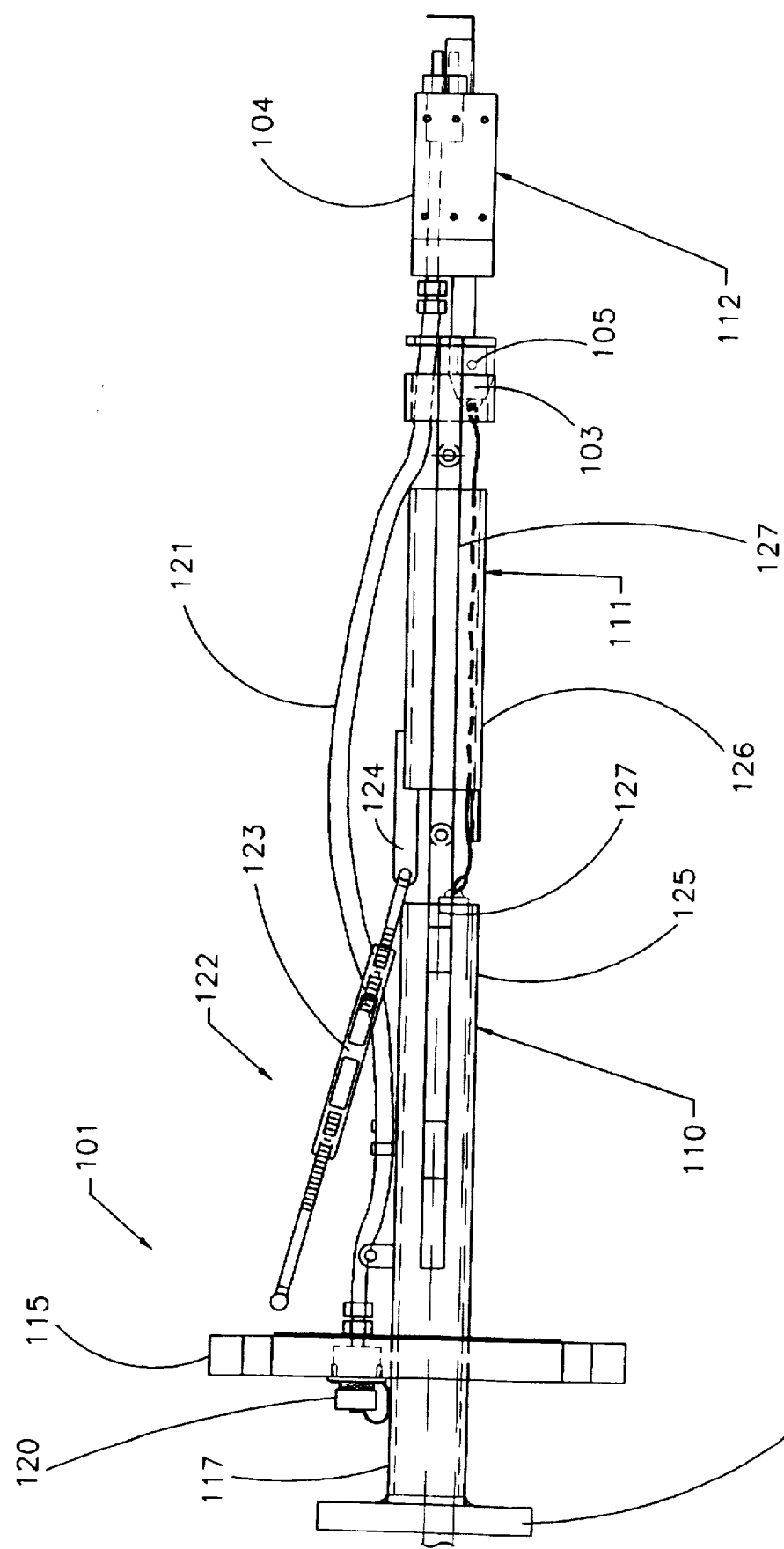
FIG. 3 is a side view of the guide assembly shown in FIG. 1.

FIGS. 2 and 3 depict top and side views of the guide arm 101, respectively. The first and second links 110 and 111 each have a tubular link body 125, 126 respectively. These tubular sections provide a path for the coupon holder 103 and the coupons 105 held thereon to travel through during removal of the coupons 105. Thus, the tubular design of the links 110, 111 (and 112 if desired) provide a path within these tubular bodies 125, 126 to the outside of the generator vessel. The flexible rod 102 is used to extend through one or more of the links 110, 111, 112 and attach to the coupon holder 103. When the rod 102 is pulled out through the desired links 110, 111, 112, the coupon holder 103 and the coupons 105 thereon are pulled through the tubular body 126, between the second and first links 111, 110, and through the first tubular body 125 and exit tubing 117 of the first link 110. In the preferred embodiment, the connecting rod 102 has a connector 129 attached to a stainless steel connecting wire 130 which is fastened to the coupon holder 103. Furthermore, the third link 112 includes a holder plate 131 upon which the coupon holder 103 resides during insertion and the monitoring process. Other embodiment may directly attach the flexible rod 102 to the coupon holder 103 to allow for insertion and removal of the coupon holder 103 while the guide arm 101 remains in place.

Notably, as shown is FIGS. 2 and 3, the link rods 127 are oppositely placed on the link bodies 125, 126 so as not to obstruct passage of the coupon holder 103 during removal, especially when the coupon holder 103 is passing from the second link 111 to the first link 110. The link bodies 125, 126 and the third link 112 each include two link rods 127 attached thereto and extending from the links 110, 111, 112 to form forked first and second hinges 113, 114. In the preferred embodiment, the link bodies 125, 126 comprise of 1 and 1/25 inch diameter stainless steel pipe and the link rods 127 are 1/8 of an inch thick by 1/2 inch wide flat bar.

Various modification of the guide arm 101 will become apparent upon a reading of this disclosure, all of these embodiments are considered part of the applicant's invention. Such modification may include embodiments incorporating a continuous tubing adapted to flex in a manner corresponding to the description above in order to navigate through the shell 405 and the shroud 406 before turning downward towards the tube sheet 409 while avoiding the tie rod 407 and the blow down line 415, or other like obstacles.

A receiving assembly 200 is adapted to mount to the exit tubing flange 119 of the guide arm 101. The receiving assembly 200 includes a first receiving tube 201 having a first receiving flange 202, a second receiving tubing 203 having a second receiving flange 204, an isolation valve 205 and an entry flange 207. An entry seal 209 is placed between the entry flange 207 and the exit flange 119. A receiving tubing seal 210 is placed between the first and second receiving tubing flanges 202, 204 for on-line monitoring.

The first receiving tubing 201, second receiving tubing 203 and the isolation valve 205 operate in conjunction to provide a tubular path for the flexible rod 102 and coupon holder 103 during monitoring and monitoring device insertion and removal. When the flexible rod 102 is pulled outwardly by the handle 210, the rod 102 and coupon holder 103 are pulled through the various tubular links of the guide arm 101 and through the path formed by the receiving assembly 200. When the coupon holder 103 passes the isolation valve 205, the isolation valve 205 is shut to effectively seal off the shell nozzle 412 to allow continued operation of the generator.

A bleed valve 211 operatively communicates with the second receiving tubing 203 to selectively drain any liquids or gases escaping into receiving assembly 200 during the removal of the coupon holder 103. A valve handle 212 connected to valve 205 is used to operate the valve.

In the preferred embodiment, a packing gland 300 coaxially attaches to the receiving assembly 200 at the first receiving tubing 201 in order to sealably engage both the receiving assembly 200 and the flexible rod 102 passing therethrough. The packing gland 300 includes a tubular gland body 301 and a series of packing washers 302 therein to sealably surround the flexible rod 102. When the washers 302 are axially compressed together, each washer radially expands to compress against the flexible rod 102 and the inside of the gland body 301. The packing gland 300 completely seals off the path leading from inside the generator vessel through the receiving assembly 200 while the flexible rod 102 is placed within the rod and guide assembly 100 and the receiving assembly 200. Furthermore, the packing gland 300 maintains this seal when the flexible rod 102 is being moved within these assemblies during the insertion or removal of the coupon holder 103. Thus, the packing gland 300 provides a movable seal about the flexible rod 102.

Applicant's have found the packing gland 300 and the flexible rod 102 optimally operate when the locking rod 102 is Teflon® or includes a Teflon® coating and the washers 302 are Teflon® coated with Garlock™. Garlock is a nonmetallic type of coating, manufactured by Garlock. Teflon® is a trademark for DuPont's tetrafluoroethylene and the many variations bearing the Teflon® name.

Preferably, the washers 302 have a wedged shaped cross-section. However, those skilled in the art will recognize that the washers 302 may be replaced by similar types of cylindrical seals providing a movable seal with respect to the flexible rod 102. Likewise, the flexible rod may comprise of any material complementary with the movable seal provided by the packing gland 300.

The movable seal formed by the packing gland 300 about the flexible rod 102 allows for the removal of the coupon holder 103 and the coupons 105 thereon while the generator is on-line. When the generator is on-line, the areas within the shell 405 are under pressure and at high operating temperatures. The monitoring system should not allow any uncontrolled leaks from this sealed environment since the fluid may be harmful to the operators.

In operation, the guide arm 101 is inserted and maneuvered in place for monitoring. Preferably, the coupon holder 103 and coupons 105, along with any other monitoring systems, are inserted along with the guide arm 101. The flexible rod 102 is likewise inserted with the other components and attached to the coupon holder 103. Once the receiving assembly 200 and the packing gland 300 are in place and sealed, the generator is brought on-line. Notably, the receiving assembly 200 is shaped to provide access within the tight quarters between the shell 405 and the barrier wall 401. The packing gland 300 may include rod adjustments 303 to lock the flexible rod 102 in position or adjust the seal formed between the washers 302 and the gland 301.

Once the generator is on-line and the coupons 105 are subjected to the cleaning or operational environment within the vessel, the coupon holder 103 is removed from within by pulling the lock rod 102 out through the packing gland 300 with handle 210. After the flexible rod 102 is removed to a point where the coupon holder 103 passes out of the guide arm 101 and the isolation valve 205, the isolation valve 205 operates is shut to seal off the guide arm 101 and the generator vessel. At this point, the coupon holder 103 is outside of the sealed environment of the generator vessel.

Any liquids or gases exiting the generator tubing during removal of the coupon holder 103 and trapped in the receiving assembly 200 after the isolation valve 205 is closed are drained through the bleed valve 211. Finally, the receiving assembly 200 is opened by separating the first receiving tubing 201 and the second receiving tubing 203 at there respective flanges 202, 204. The coupon holder 103 can be removed and the coupons 105 thereon can be analyzed.

Thus, the probe system of the present invention provides a receiving assembly adapted to provide easier access and operation in the tight quarters between the barrier wall 401 and the shell 405. Furthermore, the probe system allows placement of coupons in such difficult to access places while enabling their removal while the generator is on-line.

The present invention allows placement of corrosion monitoring electrodes and coupons in a variety of different nuclear steam generators and boilers, especially when access to the desired equipment location is via a nozzle located at a higher elevation. The concept design is easy to fabricate and operate and is modifiable to work in a large variety of generator and boiler geometries. The invention provides for positioning multiple types of corrosion monitoring equipment at a variety of locations within generators or boilers and, in particular, at any tube support plate or tube sheet, not to mention any number of location within the vessel's shroud 406 or between the shell 405 and shroud 406. The present invention also allows additional flexibility in the elevation and location of nozzles for use with such monitoring equipment.

As noted, the invention allows for an interim inspection during the chemical cleaning without process interruption. Although existing retractable type probe positioners provide this basic capability, they do not allow for retraction in tightly enclosed areas or from locations below where the positioners are installed. In sum, the invention provides the ability to perform retractions in a significantly wider variety of geometric configurations.

Certain modifications and improvements will occur to those skilled in the art upon a reading of the foregoing description. It should be understood that all such modifications and improvements have been deleted herein for the sake of conciseness and readability but are properly within the scope of the following claims.

I claim:

1. A retractable probe assembly for monitoring difficult to access areas in an substantially enclosed system, said probe assembly comprising:
    (a) a flexible rod and guide system including:
        (i) a flexible tubular guide adapted to extend through one or more barrier openings and along one of the barriers to an area to monitor in the enclosed system; and (ii) a flexible rod retractively insertable within said guide and adapted to extend through said guide having a mount for a removable monitoring device;
    (b) a receiving assembly sealably engaging said guide system and having an interior path to guide removal of said rod from said guide, said receiving assembly adapted to receive the monitoring device when removed by said rod; and
    (c) a packing gland axially connected said receiving assembly and adapted to movably engage and seal between said flexible rod and said receiving assembly, said packing gland sealing off said interior of said receiving assembly on an end opposite of said guide system.

2. The apparatus according to claim 1 wherein said packing gland includes a resilient member concentrically mounted about said rod and radially compressing against said rod to form said seal.

3. The apparatus according to claim 2 wherein said resilient member includes a plurality of resilient washers.

4. The apparatus according to claim 1 wherein said receiving assembly includes an isolation valve placed between said guide system and said receiving assembly to selectively control communication between the interior of said receiving assembly and an interior of said guide system, said guide is sealed from said interior of said receiving assembly once said rod is pulled past said isolation valve and said isolation valve is closed.

5. The apparatus according to claim 4 wherein said receiving assembly further includes a bleed valve to provide discharge of any liquids or gases trapped in said interior of said receiving assembly after said rod is removed and said isolation valve is closed.

6. The apparatus according to claim 1 wherein said receiving assembly includes an opening for access to the monitoring device once removed from the area for monitoring.

7. The apparatus according to claim 6 wherein said access is a disengagable flange assembly forming part of said receiving assembly, wherein when the flange assembly is disengaged, said receiving assembly opens and access is provided to the monitoring device.

8. A retractable probe assembly for monitoring difficult to access areas in an substantially enclosed system, said probe assembly comprising:
    (a) a flexible rod and guide system including:
        (i) a flexible tubular guide adapted to extend through one or more barrier openings and along one of the barriers to an area to monitor in the enclosed system, said guide including: a first tubular link, a second tubular link and a third tubular link; a first hinge pivotally connecting said first and second link; and a second hinge pivotally connecting said second and third link, said first and second hinge adapted to provide: a first guide orientation adapted to maintain said links of said guide in straight alignment while being held horizontally and allow said links to pivot about said hinges when said guide is axially rotated out of said first guide orientation; and a second guide orientation adapted to allow said second and third link to align along the inner wall; wherein said guide is adapted to remain in said first guide orientation while being horizontally placed through an opening in the inner and outer substantially vertically oriented wall and pivot at each said hinge along said inner wall as said guide is rotated from said first guide orientation to said second guide orientation without fully horizontally extending past said second wall; and (ii) a flexible rod retractively insertable within said guide and adapted to extend through said guide having a mount for a removable monitoring device;
    (b) a receiving assembly sealably engaging said guide system and having an interior path to guide removal of said rod from said guide, said receiving assembly adapted to receive the monitoring device when removed by said rod; and
    (c) a packing gland axially connected to said receiving assembly and adapted to movably engage and seal between said flexible rod and said receiving assembly, said packing gland sealing off the interior of said receiving assembly on an end opposite of said guide system,
    (d) wherein said packing gland includes a resilient member concentrically mounted about said rod and radially compressing against said rod to form said seal.

9. The apparatus according to claim 8 wherein said resilient member includes a plurality of resilient washers.

10. The apparatus according to claim 8 wherein said receiving assembly includes an isolation valve placed between said guide system and said receiving assembly to selectively control communication between said interior of said receiving assembly and an interior of said guide system, said guide is sealed from said interior of said receiving assembly once said rod is pulled past said isolation valve and said isolation valve is closed.

11. The apparatus according to claim 10 wherein said receiving assembly further includes a bleed valve to provide discharge of any liquids or gases trapped in said interior of said receiving assembly after said rod is removed and said isolation valve is closed.

12. The apparatus according to claim 8 wherein said receiving assembly includes an opening for access to the monitoring device once removed from the area for monitoring.

13. The apparatus according to claim 12 wherein said access is a disengagable flange assembly forming part of said receiving assembly, wherein when the flange assembly is disengaged, said receiving assembly opens and access is provided to the monitoring device.

14. The apparatus according to claim 8 wherein said guide has a second end attached to said third link, said second end of said guide having a monitor mount for mounting monitoring devices.

15. The apparatus according to claim 14 further including a cable having a plurality of conductors extending along said guide for transmitting electrical signals from said monitoring device.

16. The apparatus according to claim 15 further including a cable connector operatively associated with said cable and adapted to couple said electrical signals to a mating connector and cable.

17. The apparatus according to claim 15 wherein said cable includes a conduit which encompasses said cable for protection from corrosion or degradation.

18. The apparatus according to claim 14 further comprising a monitoring device mounted to said guide at said monitor mount wherein said monitoring device is adapted to monitor corrosion within a steam generator.

19. The apparatus according to claim 8 wherein said first link has a length sufficient to allow said first link to span between said first and second vertical wall and allow said second and third links to form said downward alignment perpendicular to said first link along said second wall.

20. The apparatus according to claim 8 further including a flexible rod having a handle at one end adapted to facilitate insertion and removal of said flexible rod through said guide and a plate wherein said guide extends therefrom, said plate adapted to cover an opening into which said guide extends.

21. The apparatus according to claim 20 wherein said plate includes a gasket adapted to form a seal between said plate and an area surrounding said opening into which said guide extends.

22. The apparatus according to claim 8 wherein said hinges are oriented to pivot in the same plane.

23. The apparatus according to claim 8 wherein said hinges are double barrel hinges.

24. The apparatus according to claim 8 wherein at least one of said links of said guide are adapted to vary in length in order to adapt to various geometries of said walls.

25. The apparatus according to claim 8 wherein said guide further includes a locking rod connected between said first tubular link and said second tubular link to control the swing of said guide.

26. The apparatus according to claim 25 wherein said locking rod includes turnbuckle assembly to provide length adjustment of said locking rod.

* * * * *